(12) United States Patent
Hellyer et al.

(10) Patent No.: US 6,207,818 B1
(45) Date of Patent: Mar. 27, 2001

(54) **AMPLIFICATION AND DETECTION OF SHIGELLA SPP. AND ENTEROINVASIVE STRAINS OF *ESCHERICHIA COLI***

(75) Inventors: Tobin J. Hellyer, Owings Mills; Ray A. McMillian, Timonium, both of MD (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 09/503,859

(22) Filed: Feb. 14, 2000

Related U.S. Application Data

(62) Division of application No. 09/289,750, filed on Apr. 12, 1999, now Pat. No. 6,060,252.

(51) Int. Cl.[7] .................................................. C07H 21/02
(52) U.S. Cl. ................... 536/24.3; 536/24.32; 536/24.33
(58) Field of Search ............................... 435/6; 536/23.1, 536/24.3

(56) References Cited

U.S. PATENT DOCUMENTS

| | | | |
|---|---|---|---|
| 5,627,275 | 5/1997 | Roll | 536/23.7 |
| 5,705,332 | 1/1998 | Roll | 435/6 |
| 5,795,717 | * 8/1998 | Nakayama et al. | 435/6 |

OTHER PUBLICATIONS

Islam, M.S. et al., "Use of Polymerase Chain Reaction and Fluorescent–Antibody Methods for Detecting Viable but Nonculturable *Shigella dysenteriae* Type 1 in Laboratory Microcosms", Applied and Environmental Microbiology, vol. 59, pp. 536–540 (1993).*

Oberhelman, R.A. et al. "Evaluation of Alkaline Phosphatase–Labelled ipaH Probe for Diagnosis of Shigella Infections", J. Clinical Microbiology, vol. 31, pp. 2101–2104 (1993).*

Buysse, J.M. et al., "Genetic polymorphism of the ipaH multicopy antigen gene in Shigella spps. and enteroinvasive *Escherichia coli*", Microbial Pthogenesis, vol. 19, pp. 335–349 (1995).*

Wang, Rong–Fu et al., "Phylogenetic analysis and identification of Shigella spp. by molecular probes", Molecular and Cellular Probes, vol. 11, pp. 427–432 (1997).*

Walker, G. et al., Proc. Natl. Acad. Sci USA 89:392–396 (1992).

Walker, G. et. al. Nucl. Acids Res. 20:1691–1696 (1992).

* cited by examiner

*Primary Examiner*—Kenneth R. Horlick
*Assistant Examiner*—Teresa Strzelecka
(74) *Attorney, Agent, or Firm*—David W. Highet

(57) ABSTRACT

Amplification primers and methods for specific amplification and detection of a Shigella spp. and enteroinvasive stains of *Escherichia coli* (EIEC) target are disclosed. The primer-target binding sequences are useful for amplification and detection of Shigella and EIEC target in a variety of amplification and detection reactions.

11 Claims, No Drawings

AMPLIFICATION AND DETECTION OF SHIGELLA SPP. AND ENTEROINVASIVE STRAINS OF ESCHERICHIA COLI

This is a division of U.S. patent application Ser. No. 09/289,750, filed Apr. 12, 1999, U.S. Pat. No. 6,060,252.

FIELD OF THE INVENTION

The present invention relates to methods for determining the presence or absence of Shigella spp. and enteroinvasive strains of Escherichia coli (EIEC) in patients, food or water. The method involves using nucleic acid primers to amplify specifically a Shigella and EIEC ipaH target, preferably using one of the techniques of Strand Displacement Amplification (SDA), thermophilic Strand Displacement Amplification (tSDA) or fluorescent real time tSDA, and optionally using a microelectronic array.

BACKGROUND OF THE INVENTION

Organisms of the genus Shigella cause classic bacillary dysentery that is characterized by severe diarrhea and abdominal pain. Shigella spp. are typically associated with self-limiting infections that are rarely fatal except in children or the elderly. However, infection with *S. dysenteriae* can cause a severe form of the disease with up to 20% of cases proving fatal. Like Shigella spp., EIEC causes enteritis with fever, abdominal cramps and watery diarrhea. Strains of EIEC are, however, considered to be rare both in the developed and developing world. Nucleic acid amplification is a powerful technology that facilitates rapid detection of specific target sequences. It is therefore a promising technology for the rapid detection and identification of Shigella spp. and EIEC. The oligonucleotide primers of the present invention are applicable to the amplification and detection of Shigella- and EIEC-specific regions of the ipaH virulence gene. The ipaH gene is approximately 16 kb in length and is found in multiple copies on both the large virulence-associated plasmid of Shigella spp. and the bacterial chromosome.

The following terms are defined herein as follows:

An amplification primer is a primer for amplification of a target sequence by extension of the primer after hybridization to the target sequence. Amplification primers are typically about 10–75 nucleotides in length, preferably about 15–50 nucleotides in length. The total length of an amplification primer for SDA is typically about 25–50 nucleotides. The 3' end of an SDA amplification primer (the target binding sequence) hybridizes at the 3' end of the target sequence. The target binding sequence is about 10–25 nucleotides in length and confers hybridization specificity on the amplification primer. The SDA amplification primer further comprises a recognition site for a restriction endonuclease 5' to the target binding sequence. The recognition site is for a restriction endonuclease which will nick one strand of a DNA duplex when the recognition site is hemimodified, as described by G. Walker, et al. (1992. *Proc. Natl. Acad. Sci. USA* 89:392–396 and 1992 *Nucl. Acids Res.* 20:1691–1696). The nucleotides 5' to the restriction endonuclease recognition site (the "tail") function as a polymerase repriming site when the remainder of the amplification primer is nicked and displaced during SDA. The repriming function of the tail nucleotides sustains the SDA reaction and allows synthesis of multiple amplicons from a single target molecule. The tail is typically about 10–25 nucleotides in length. Its length and sequence are generally not critical and can be routinely selected and modified. As the target binding sequence is the portion of a primer which determines its target-specificity, for amplification methods which do not require specialized sequences at the ends of the target the amplification primer generally consists essentially of only the target binding sequence. For example, amplification of a target sequence according to the invention using the Polymerase Chain Reaction (PCR) will employ amplification primers consisting of the target binding sequences of the amplification primers described herein. For amplification methods that require specialized sequences appended to the target other than the nickable restriction endonuclease recognition site and the tail of SDA (e.g., an RNA polymerase promoter for Self-Sustained Sequence Replication (3SR), Nucleic Acid Sequence-Based Amplification (NASBA) or the Transcription-Based Amplification System (TAS)), the required specialized sequence may be linked to the target binding sequence using routine methods for preparation of oligonucleotides without altering the hybridization specificity of the primer.

A bumper primer or external primer is a primer used to displace primer extension products in isothermal amplification reactions. The bumper primer anneals to a target sequence upstream of the amplification primer such that extension of the bumper primer displaces the downstream amplification primer and its extension product.

The terms target or target sequence refer to nucleic acid sequences to be amplified. These include the original nucleic acid sequence to be amplified, the complementary second strand of the original nucleic acid sequence to be amplified and either strand of a copy of the original sequence which is produced by the amplification reaction. These copies serve as amplifiable targets by virtue of the fact that they contain copies of the sequence to which the amplification primers hybridize.

Copies of the target sequence which are generated during the amplification reaction are referred to as amplification products, amplimers or amplicons.

The term extension product refers to the copy of a target sequence produced by hybridization of a primer and extension of the primer by polymerase using the target sequence as a template.

The term species-specific refers to detection, amplification or oligonucleotide hybridization to a species of organism or a group of related species without substantial detection, amplification or oligonucleotide hybridization to other species of the same genus or species of a different genus.

The term assay probe refers to any oligonucleotide used to facilitate detection or identification of a nucleic acid. Detector probes, detector primers, capture probes, signal primers and reporter probes as described below are examples of assay probes.

The term amplicon refers to the product of the amplification reaction generated through the extension of either or both of a pair of amplification primers. An amplicon may contain exponentially amplified nucleic acids if both primers utilized hybridize to a target sequence. Alternatively, amplicons may be generated by linear amplification if one of the primers utilized does not hybridize to the target sequence. Thus, this term is used generically herein and does not imply the presence of exponentially amplified nucleic acids.

A microelectronic array (or electronic microarray) is a device with an array of electronically self-addressable microscopic locations. Each microscopic location contains an underlying working direct current (DC) micro-electrode supported by a substrate. The surface of each micro location has a permeation layer for the free transport of small counter-ions, and an attachment layer for the covalent coupling of specific binding entities.

An array or matrix is an arrangement of locations on the device. The locations can be arranged in two dimensional arrays, three dimensional arrays, or other matrix formats. The number of locations can range from several to at least hundreds of thousands.

Electronic addressing (or targeting) is the placement of charged molecules at specific test sites. Since DNA has a strong negative charge, it can be electronically moved to an area of positive charge. A test site or a row of test sites on the microchip is electronically activated with a positive charge. A solution of DNA probes is introduced onto the microchip. The negatively charged probes rapidly move to the positively charged sites, where they concentrate and are chemically bound to that site. The microchip is then washed and another solution of distinct DNA probes can be added. Site by site, row by row, an array of specifically bound DNA probes can be assembled or addressed on the microchip. With the ability to electronically address capture probes to specific sites, the system allows the production of custom arrays through the placement of specific capture probes on a microchip. In this connection, the term "electronically addressable" refers to a capacity of a microchip to direct materials such as nucleic acids and enzymes and other amplification components from one position to another on the microchip by electronic biasing of the capture sites of the chip. "Electronic biasing" is intended to mean that the electronic charge at a capture site or another position on the microchip may be manipulated between a net positive and a net negative charge so that molecules in solution and in contact with the microchip may be directed toward or away from one position on the microchip or form one position to another.

Electronic concentration and hybridization uses electronics to move and concentrate target molecules to one or more test sites (or capture sites) on the microchip. The electronic concentration of sample DNA at each test site promotes rapid hybridization of sample DNA with complementary capture probes. In contrast to the passive hybridization process, the electronic concentration process has the distinct advantage of significantly accelerating the rate of hybridization. To remove any unbound or nonspecifically bound DNA from each site, the polarity or charge of the site is reversed to negative, thereby forcing any unbound or nonspecifically bound DNA back into solution away from the capture probes. In addition, since the test molecules are electronically concentrated over the test site, a lower concentration of target DNA molecules is required, thus reducing the time and labor otherwise required for pre-test sample preparation. The term "capture site" refers to a specific position on an electronically addressable microchip wherein electronic biasing is initiated and where molecules such as nucleic acid probes and target molecules are attracted or addressed by such biasing.

Electronic stringency control is the reversal of electrical potential to remove unbound and nonspecifically bound DNA quickly and easily as part of the hybridization process. Electronic stringency provides quality control for the hybridization process and ensures that any bound pairs of DNA are truly complementary. The precision, control, and accuracy of platform technology, through the use of the controlled delivery of current in the electronic stringency process, permits the detection of single point mutations, single base pair mismatches, or other genetic mutations, which may have significant implications in a number of diagnostic and research applications. Electronic stringency is achieved without the cumbersome processing and handling otherwise required to achieve the same results through conventional methods. In contrast to passive arrays, this technology can accommodate both short and long single-stranded fragments of DNA. The use of longer probes increases the certainty that the DNA which hybridizes with the capture probe is the correct target. Electronic stringency control reduces the required number of probes and therefore test sites on the microchip, relative to conventional DNA arrays. In contrast, traditional passive hybridization processes are difficult to control and require more replicants of every possible base pair match so that correct matches can be positively identified.

Electronic multiplexing allows the simultaneous analysis of multiple tests from a single sample. Electronic multiplexing is facilitated by the ability to control individual test sites independently (for addressing of capture probes or capture molecules and concentration of test sample molecules) which allows for the simultaneous use of biochemically unrelated molecules on the same microchip. Sites on a conventional DNA array cannot be individually controlled, and therefore the same process steps must be performed on the entire array. The use of electronics in this technology provides increased versatility and flexibility over such conventional methods.

SUMMARY OF THE INVENTION

The present invention provides oligonucleotide primers that can be used for amplification of target sequences found in Shigella spp. and EIEC. More specifically, the target sequence comprises segments of the ipaH gene. The amplification primers have been designed for high-efficiency, high-specificity amplification at elevated temperatures, such as in tSDA and the PCR, however, they are also useful in lower-temperature amplification reactions such as conventional SDA, 3SR or NASBA. Oligonucleotide assay probes that hybridize to the assay region of the amplified target are used to detect the amplification products.

The oligonucleotides of the invention may be used after culture as a means for confirming the identity of the cultured organism. Alternatively, they may be used with clinical samples from humans or animals, such as fecal material or urine, or with samples of contaminated food or water for detection and identification of Shigella spp.s' and EIECs' nucleic acid using known amplification methods. In either case, the inventive oligonucleotides and assay methods provide a means for rapidly discriminating between Shigella spp. and EIEC and other microorganisms, allowing the practitioner to identify this microorganism rapidly without resorting to the more traditional procedures customarily relied upon. Such rapid identification of the specific etiological agent involved in an infection provides information that can be used to determine appropriate action within a short period of time.

SUMMARY OF THE SEQUENCES

SEQ ID NOs:1–3 are sequences of oligonucleotides used as upstream primers for amplification of the ipaH virulence gene. SEQ ID NOs:4–6 are sequences of oligonucleotides used as downstreams primers for amplification of the ipaH virulence gene. SEQ ID NO:7 is the sequence of an oligonucleotide used as an upstream bumper for SDA amplification. SEQ ID NO:8 is the sequence of an oligonucleotide used as a downstream bumper for SDA amplification. SEQ ID NOs:9–10 are sequences of detector oligonucleotides (probes or reporters) for the ipaH virulence gene.

DETAILED DESCRIPTION OF THE INVENTION

The present invention relates to oligonucleotides, amplification primers and assay probes which exhibit Shigella and EIEC specificity in nucleic acid amplification reactions. Also provided are methods for detecting and identifying Shigella spp.s' and EIECs' nucleic acids using the oligonucleotides of the invention. The preferred methods are to use SDA, tSDA or homogeneous real time fluorescent tSDA. These methods are known to those skilled in the art from references such as U.S. Pat. No. 5,547,861, U.S. Pat. No. 5,648,211, U.S. Pat. No. 5,846,726 and U.S. patent application Ser. No. 08/865,675, filed May 30, 1997, the disclosures of which are hereby specifically incorporated herein by reference. The use of microelectronic arrays for the analysis of nucleic acids are known to those skilled in the art from references such as U.S. Pat. No. 5,605,662 and U.S. Pat. No. 5,632,957 and PCT published application Nos. WO 96/01836 and WO 97/12030.

The primers of the present invention were designed based on an analysis of the ipaH virulence gene of Shigella spp. and EIEC to identify Shigella- and EIEC-specific regions. Primers developed for use in SDA are shown in Table 1. Also shown are probes for the detection of the resultant amplicons. The exemplary restriction endonuclease recognition sites (BsoBI) in the amplification primers are shown in boldface type and the target binding sequences are italicized. The target binding sequence of an amplification primer determines its target specificity.

conditions to maintain Shigella- and EIEC-specificity require only routine experimentation and are within the ordinary skill in the art.

The amplification products generated using the primers disclosed herein may be detected by a characteristic size, for example, on polyacrylamide or agarose gels stained with ethidium bromide. Alternatively, amplified target sequences may be detected by means of an assay probe, which is an oligonucleotide tagged with a detectable label. In one embodiment, at least one tagged assay probe may be used for detection of amplified target sequences by hybridization (a detector probe), by hybridization and extension as described by Walker, et al. (1992, *Nucl. Acids Res.* 20:1691–1696) (a detector primer) or by hybridization, extension and conversion to double stranded form as described in EP 0 678 582 (a signal primer). SEQ ID NO:9 and SEQ ID NO:10 are particularly useful as detector primers, i.e., primer extension detector probes, in conjunction with the amplification primers of the invention for detection of Shigella spp. and EIEC. Preferably, the assay probe is selected to hybridize to a sequence in the target that is between the amplification primers, i.e., it should be an internal assay probe. Alternatively, an amplification primer or the target binding sequence thereof may be used as the assay probe.

The detectable label of the assay probe is a moiety which can be detected either directly or indirectly as an indication of the presence of the target nucleic acid. For direct detection of the label, assay probes may be tagged with a radioisotope and detected by autoradiography or tagged with a fluores-

TABLE 1

| Amplification Oligonucleotides | | |
|---|---|---|
| Upstream Primers | | |
| ShH1AL48: | 5'-CGATTCCGCTCCAGACTTCTCGGG*TCAGAAGCCGTGAAGA* | (SEQ ID 1) |
| ShH1AL46: | 5'-CGATTCCGCTCCAGACTTCTCGGG*TCAGAAGCCGTGAAG* | (SEQ ID 2) |
| ShH1AL44: | 5'-CGATTCCGCTCCAGACTTCTCGGG*CAGAAGCCGTGAAG* | (SEQ ID 3) |
| Downstream Primers | | |
| ShH1AR50: | 5'-ACCGCATCGAAGTCATGTCTCGGG*GCCATGGTCCCCAGA* | (SEQ ID 4) |
| ShH1AR46: | 5'-ACCGCATCGAAGTCATGTCTCGGG*CATGGTCCCCAGAG* | (SEQ ID 5) |
| ShH1AR42: | 5'-ACCGCATCGAAGTCATGTCTCGGG*CATGGTCCCCAGA* | (SEQ ID 6) |
| Upstream Bumper | | |
| ShH1BL44: | 5'-GCACTGCCGAAGC | (SEQ ID 7) |
| Downstream Bumper | | |
| ShH1BBR44: | 5'-GCTTCAGTACAGCAT | (SEQ ID 8) |
| Detector Probes | | |
| Sh1DL44: | 5'-GAATTTACGGACTGG | (SEQ ID 9) |
| Sh1DR46: | 5'-GAACCAGTCCGTAAAT | (SEQ ID 10) |

As nucleic acids do not require complete complementarity in order to hybridize, it is to be understood that the probe and primer sequences herein disclosed may be modified to some extent without loss of utility as Shigella- and EIEC-specific probes and primers. As is known in the art, hybridization of complementary and partially complementary nucleic acid sequences may be obtained by adjustment of the hybridization conditions to increase or decrease stringency (i.e., adjustment of hybridization pH, temperature or salt content of the buffer). Such minor modifications of the disclosed sequences and any necessary adjustments of hybridization cent moiety and detected by fluorescence as is known in the art. Alternatively, the assay probes may be indirectly detected by tagging with a label that requires additional reagents to render it detectable. Indirectly detectable labels include, for example, chemiluminescent agents, enzymes that produce visible reaction products and ligands (e.g., haptens, antibodies or antigens) which may be detected by binding to labeled specific binding partners (e.g., antibodies or antigens/haptens). Ligands are also useful for immobilizing the ligand-labeled oligonucleotide (the capture probe) on a solid phase to facilitate its detection. Particularly useful labels include biotin (detectable by binding to labeled avidin or streptavidin) and enzymes such as horseradish peroxidase or alkaline phosphatase (detectable by addition of enzyme substrates to produce colored reaction products). Methods for adding such labels to, or including such labels in, oligonucleotides are well known in the art and any of these methods are suitable for use in the present invention.

Examples of specific detection methods which may be employed include a chemiluminescent method in which amplified products are detected using a biotinylated capture probe and an enzyme-conjugated detector probe as described in U.S. Pat. No. 5,470,723. After hybridization of these two assay probes to different sites in the assay region of the target sequence (between the binding sites of the two amplification primers), the complex is captured on a streptavidin-coated microtiter plate by means of the capture probe, and the chemiluminescent signal is developed and read in a luminometer. As another alternative for detection of amplification products, a signal primer as described in EP 0 678 582 may be included in the SDA reaction. In this embodiment, labeled secondary amplification products are generated during SDA in a target amplification-dependent manner and may be detected as an indication of target amplification by means of the associated label.

For commercial convenience, amplification primers for specific detection and identification of nucleic acids may be packaged in the form of a kit. Typically, such a kit contains at least one pair of amplification primers. Reagents for performing a nucleic acid amplification reaction may also be included with the target-specific amplification primers, for example, buffers, additional primers, nucleotide triphosphates, enzymes, etc. The components of the kit are packaged together in a common container, optionally including instructions for performing a specific embodiment of the inventive methods. Other optional components may also be included in the kit, e.g., an oligonucleotide tagged with a label suitable for use as an assay probe, and/or reagents or means for detecting the label.

The target binding sequences of the amplification primers confer species hybridization specificity on the oligonucleotides and therefore provide species specificity to the amplification reaction. Thus, the target binding sequences of the amplification primers of the invention are also useful in other nucleic acid amplification protocols such as the PCR, conventional SDA (a reaction scheme which is essentially the same as that of tSDA but conducted at lower temperatures using mesophilic enzymes), 3SR, NASBA and TAS. Specifically, any amplification protocol which utilizes cyclic, specific hybridization of primers to the target sequence, extension of the primers using the target sequence as a template and separation or displacement of the extension products from the target sequence may employ the target binding sequences of the invention. For amplification methods that do not require specialized, non-target binding sequences (e.g., PCR), the amplification primers may consist only of the target binding sequences of the amplification primers listed in Table 1.

Other sequences, as required for performance of a selected amplification reaction, may optionally be added to the target binding sequences disclosed herein without altering the species specificity of the oligonucleotide. By way of example, the specific amplification primers may contain a recognition site for the restriction endonuclease BsoBI which is nicked during the SDA reaction. It will be apparent to one skilled in the art that other nickable restriction endonuclease recognition sites may be substituted for the BsoBI recognition site including, but not limited to, those recognition sites disclosed in EP 0 684 315. Preferably, the recognition site is for a thermophilic restriction endonuclease so that the amplification reaction may be performed under the conditions of tSDA. Similarly, the tail sequence of the amplification primer (5' to the restriction endonuclease recognition site) is generally not critical, although the restriction site used for SDA and sequences which will hybridize either to their own target binding sequence or to the other primers should be avoided. Some amplification primers for SDA therefore consist of 3' target binding sequences, a nickable restriction endonuclease recognition site 5' to the target binding sequence and a tail sequence about 10–25 nucleotides in length 5' to the restriction endonuclease recognition site. The nickable restriction endonuclease recognition site and the tail sequence are sequences required for the SDA reaction. For other amplification reactions (e.g., 3SR, NASBA and TAS), the amplification primers may consist of the target binding sequence and additional sequences required for the selected amplification reaction (e.g., sequences required for SDA as described above or a promoter recognized by RNA polymerase for 3SR). Adaptation of the target binding sequences of the invention to amplification methods other than SDA employs routine methods for preparation of amplification primers, such as chemical synthesis, and the well known structural requirements for the primers of the selected amplification reaction. The target binding sequences of the invention may therefore be readily adapted to Shigella- and EIEC-specific target amplification and detection in a variety of amplification reactions using only routine methods for production, screening and optimization.

In SDA, the bumper primers are not essential for species specificity, as they function to displace the downstream, species-specific amplification primers. It is required only that the bumper primers hybridize to the target upstream from the amplification primers so that when they are extended they will displace the amplification primer and its extension product. The particular sequence of the bumper primer is therefore generally not critical, and may be derived from any upstream target sequence which is sufficiently close to the binding site of the amplification primer to allow displacement of the amplification primer extension product upon extension of the bumper primer. Occasional mismatches with the target in the bumper primer sequence or some cross-hybridization with non-target sequences do not generally negatively affect amplification efficiency as long as the bumper primer remains capable of hybridizing to the specific target sequence.

Amplification reactions employing the primers of the invention may incorporate thymine as taught by Walker, et al. (1992, *Nucl. Acids Res.* 20:1691–1696), or they may wholly or partially substitute 2'-deoxyuridine 5'-triphosphate for TTP in the reaction to reduce cross-contamination of subsequent amplification reactions, e.g., as taught in EP 0 624 643. dU (uridine) is incorporated into amplification products and can be excised by treatment with uracil DNA glycosylase (UDG). These abasic sites render the amplification product unamplifiable in subsequent amplification reactions. UDG may be inactivated by uracil DNA glycosylase inhibitor (UGI) prior to performing the subsequent amplification to prevent excision of dU in newly-formed amplification products.

SDA is an isothermal method of nucleic acid amplification in which extension of primers, nicking of a hemimodified restriction endonuclease recognition/cleavage site, displacement of single stranded extension products, annealing of primers to the extension products (or the original target sequence) and subsequent extension of the primers occurs concurrently in the reaction mix. This is in contrast to PCR, in which the steps of the reaction occur in discrete phases or cycles as a result of the temperature cycling characteristics of the reaction. SDA is based upon 1) the ability of a restriction endonuclease to nick the unmodified strand of a hemiphosphorothioate form of its double stranded recognition/cleavage site and 2) the ability of certain polymerases to initiate replication at the nick and displace the downstream non-template strand. After an initial incubation at increased temperature (about 95° C.) to denature double stranded target sequences for annealing of the primers, subsequent polymerization and displacement of newly synthesized strands takes place at a constant temperature. Production of each new copy of the target sequence consists of five steps: 1) binding of amplification primers to an original target sequence or a displaced single-stranded extension product previously polymerized, 2) extension of the primers by a 5'-3' exonuclease deficient polymerase incorporating an α-thio deoxynucleoside triphosphate (α-thio dNTP), 3) nicking of a hemimodified double stranded restriction site, 4) dissociation of the restriction enzyme from the nick site, and 5) extension from the 3' end of the nick by the 5'-3' exonuclease deficient polymerase with displacement of the downstream newly synthesized strand. Nicking, polymerization and displacement occur concurrently and continuously at a constant temperature because extension from the nick regenerates another nickable restriction site. When a pair of amplification primers is used, each of which hybridizes to one of the two strands of a double stranded target sequence, amplification is exponential. This is because the sense and antisense strands serve as templates for the opposite primer in subsequent rounds of amplification. When a single amplification primer is used, amplification is linear because only one strand serves as a template for primer extension. Examples of restriction endonucleases which nick their double stranded recognition/cleavage sites when an α-thio dNTP is incorporated are HincII, HindII, AvaI, NciI and Fnu4HI. All of these restriction endonucleases and others which display the required nicking activity are suitable for use in conventional SDA. However, they are relatively thermolabile and lose activity above about 40° C.

Targets for amplification by SDA may be prepared by fragmenting larger nucleic acids by restriction with an endonuclease which does not cut the target sequence. However, it is generally preferred that target nucleic acids having selected restriction endonuclease recognition/cleavage sites for nicking in the SDA reaction be generated as described by Walker, et al. (1992, *Nucl. Acids Res.* 20:1691–1696) and in U.S. Pat. No. 5,270,184 (herein incorporated by reference). Briefly, if the target sequence is double stranded, four primers are hybridized to it. Two of the primers ($S_1$ and $S_2$) are SDA amplification primers and two ($B_1$ and $B_2$) are external or bumper primers. $S_1$ and $S_2$ bind to opposite strands of double stranded nucleic acids flanking the target sequence. $B_1$ and $B_2$ bind to the target sequence 5' (i.e., upstream) of $S_1$ and $S_2$, respectively. The exonuclease deficient polymerase is then used to simultaneously extend all four primers in the presence of three deoxynucleoside triphosphates and at least one modified deoxynucleoside triphosphate (e.g., 2'-deoxyadenosine 5'-O-(1-thiotriphosphate), "dATPαS"). The extension products of $S_1$ and $S_2$ are thereby displaced from the original target sequence template by extension of $B_1$ and $B_2$. The displaced, single stranded extension products of the amplification primers serve as targets for binding of the opposite amplification and bumper primer (e.g., the extension product of $S_1$ binds $S_2$ and $B_2$). The next cycle of extension and displacement results in two double stranded nucleic acid fragments with hemimodified restriction endonuclease recognition/cleavage sites at each end. These are suitable substrates for amplification by SDA. As in SDA, the individual steps of the target generation reaction occur concurrently and continuously, generating target sequences with the recognition/cleavage sequences at the ends required for nicking by the restriction enzyme in SDA. As all of the components of the SDA reaction are already present in the target generation reaction, target sequences generated automatically and continuously enter the SDA cycle and are amplified.

To prevent cross-contamination of one SDA reaction by the amplification products of another, dUTP may be incorporated into SDA-amplified DNA in place of dTTP without inhibition of the amplification reaction. The uracil-modified nucleic acids may then be specifically recognized and inactivated by treatment with uracil DNA glycosylase (UDG). Therefore, if dUTP is incorporated into SDA-amplified DNA in a prior reaction, any subsequent SDA reactions can be treated with UDG prior to amplification of double stranded targets, and any dU containing DNA from previously amplified reactions will be rendered unamplifiable. The target DNA to be amplified in the subsequent reaction does not contain dU and will not be affected by the UDG treatment. UDG may then be inhibited by treatment with UGI prior to amplification of the target. Alternatively, UDG may be heat-inactivated. In tSDA, the higher temperature of the reaction itself ($\geq 50°$ C.) can be used concurrently to inactivate UDG and amplify the target.

SDA requires a polymerase which lacks 5'-3' exonuclease activity, initiates polymerization at a single stranded nick in double stranded nucleic acids, and displaces the strand downstream of the nick while generating a new complementary strand using the unnicked strand as a template. The polymerase must extend by adding nucleotides to a free 3'-OH. To optimize the SDA reaction, it is also desirable that the polymerase be highly processive to maximize the length of target sequence which can be amplified. Highly processive polymerases are capable of polymerizing new strands of significant length before dissociating and terminating synthesis of the extension product. Displacement activity is essential to the amplification reaction, as it makes the target available for synthesis of additional copies and generates the single stranded extension product to which a second amplification primer may hybridize in exponential amplification reactions. Nicking activity of the restriction enzyme is also of great importance, as it is nicking which perpetuates the reaction and allows subsequent rounds of target amplification to initiate.

tSDA is performed essentially as the conventional SDA described by Walker, et al. (1992, *Proc. Natl. Acad. Sci. USA* 89:392–396 and 1992, *Nucl. Acids Res.* 20:1691–1696), with substitution of the desired thermostable polymerase and thermostable restriction endonuclease. Of course, the temperature of the reaction will be adjusted to the higher temperature suitable for the substituted enzymes and the HincII restriction endonuclease recognition/cleavage site will be replaced by the appropriate restriction endonuclease recognition/cleavage site for the selected thermostable endonuclease. Also in contrast to Walker, et al., the practitioner may include the enzymes in the reaction mixture prior to the initial denaturation step if they are sufficiently stable at the denaturation temperature. Preferred restriction endonucleases for use in thermophilic SDA are BsrI, BstNI, BsmAI, BslI and BsoBI (New England BioLabs), and BstOI (Promega). The preferred thermophilic polymerases are Bca (Panvera) and Bst (New England Biolabs).

Homogeneous real time fluorescent tSDA is a modification of tSDA. It employs detector oligonucleotides to produce reduced fluorescence quenching in a target-dependent manner. The detector oligonucleotides contain a donor/acceptor dye pair linked such that fluorescence quenching occurs in the absence of target. Unfolding or linearization of an intramolecularly base-paired secondary structure in the detector oligonucleotide in the presence of the target increases the distance between the dyes and reduces fluorescence quenching. Unfolding of the base-paired secondary structure typically involves intermolecular base-pairing between the sequence of the secondary structure and a complementary strand such that the secondary structure is at least partially disrupted. It may be fully linearized in the presence of a complementary strand of sufficient length. In a preferred embodiment, a restriction endonuclease recognition site (RERS) is present between the two dyes such that intermolecular base-pairing between the secondary structure and a complementary strand also renders the RERS double-stranded and cleavable or nickable by a restriction endonuclease. Cleavage or nicking by the restriction endonuclease separates the donor and acceptor dyes onto separate nucleic acid fragments, further contributing to decreased quenching. In either embodiment, an associated change in a fluorescence parameter (e.g., an increase in donor fluorescence intensity, a decrease in acceptor fluorescence intensity or a ratio of fluorescence before and after unfolding) is monitored as an indication of the presence of the target sequence. Monitoring a change in donor fluorescence intensity is preferred, as this change is typically larger than the change in acceptor fluorescence intensity. Other fluorescence parameters such as a change in fluorescence lifetime may also be monitored.

A detector oligonucleotide for homogeneous real time fluorescent tSDA is an oligonucleotide which comprises both a single-stranded 5' or 3' section which hybridizes to the target sequence (the target binding sequence), as well as an intramolecularly base-paired secondary structure adjacent to the target binding sequence. The detector oligonucleotides of the invention further comprise a donor/acceptor dye pair linked to the detector oligonucleotide such that donor fluorescence is quenched when the secondary structure is intramolecularly base-paired and unfolding or linearization of the secondary structure results in a decrease in fluorescence quenching. Cleavage of an oligonucleotide refers to breaking the phosphodiester bonds of both strands of a DNA duplex or breaking the phosphodiester bond of single-stranded DNA. This is in contrast to nicking, which refers to breaking the phosphodiester bond of only one of the two strands in a DNA duplex.

The detector oligonucleotides of the invention for homogeneous real time fluorescent tSDA comprise a sequence which forms an intramolecularly base-paired secondary structure under the selected reaction conditions for primer extension or hybridization. The secondary structure is positioned adjacent to the target binding sequence of the detector oligonucleotide so that at least a portion of the target binding sequence forms a single-stranded 3' or 5' tail. As used herein, the term "adjacent to the target binding sequence" means that all or part of the target binding sequence is left single-stranded in a 5' or 3' tail which is available for hybridization to the target. That is, the secondary structure does not comprise the entire target binding sequence. A portion of the target binding sequence may be involved in the intramolecular base-pairing in the secondary structure, it may include all or part of a first sequence involved in intramolecular base-pairing in the secondary structure, it may include all or part of a first sequence involved in intramolecular base-pairing in the secondary structure but preferably does not extend into its complementary sequence. For example, if the secondary structure is a stem-loop structure (e.g., a "hairpin") and the target binding sequence of the detector oligonucleotide is present as a single-stranded 3' tail, the target binding sequence may also extend through all or part of the first arm of the stem and, optionally, through all or part of the loop. However, the target binding sequence preferably does not extend into the second arm of the sequence involved in stem intramolecular base-pairing. That is, it is desirable to avoid having both sequences involved in intramolecular base-pairing in a secondary structure capable of hybridizing to the target. Mismatches in the intramolecularly base-paired portion of the detector oligonucleotide secondary structure may reduce the magnitude of the change in fluorescence in the presence of target but are acceptable if assay sensitivity is not a concern. Mismatches in the target binding sequence of the single-stranded tail are also acceptable but may similarly reduce assay sensitivity and/or specificity. However, it is a feature of the present invention that perfect base-pairing in both the secondary structure and the target binding sequence do not compromise the reaction. Perfect matches in the sequences involved in hybridization improve assay specificity without negative effects on reaction kinetics.

When added to the amplification reaction, the detector oligonucleotide signal primers of the invention are converted to double-stranded form by hybridization and extension as described above. Strand displacement by the polymerase also unfolds or linearizes the secondary structure and converts it to double-stranded from by synthesis of a complementary strand. The RERS, if present, also becomes double-stranded and cleavable or nickable by the restriction endonuclease. As the secondary structure is unfolded or linearized by the strand displacing activity of the polymerase, the distance between the donor and acceptor dye is increased, thereby reducing quenching of donor fluorescence. The associated change in fluorescence of either the donor or acceptor dye may be monitored or detected as an indication of amplification of the target sequence. Cleavage or nicking of the RERS generally further increases the magnitude of the change in fluorescence by producing two separate fragments of the double-stranded secondary amplification product, each having one of the two dyes linked to it. These fragments are free to diffuse in the reaction solution, further increasing the distance between the dyes of the donor/acceptor pair. An increase in donor fluorescence intensity or a decrease in acceptor fluorescence intensity may be detected and/or monitored as an indication that target amplification is occurring or has occurred, but other fluorescence parameters which are affected by the proximity of the donor/acceptor dye pair may also be monitored. A change in fluorescence intensity of the donor or acceptor may also be detected as a change in a ratio of donor and/or acceptor fluorescence intensities. For example, a change in fluorescence intensity may be detected as; a) an increase in the ratio of donor fluorophore fluorescence after linearizing or unfolding the secondary structure and donor fluorophore fluorescence in the detector oligonucleotide prior to linearizing or unfolding, or b) as a decrease in the ratio of acceptor dye fluorescence after linearizing or unfolding and acceptor dye fluorescence in the detector oligonucleotide prior to linearizing or unfolding.

It will be apparent that, in addition to SDA, the detector oligonucleotides of the invention may be adapted for use as signal primers in other primer extension amplification methods (e.g., PCR, 3SR, TMA or NASBA). For example, the methods may be adapted for use in PCR by using PCR amplification primers and a strand displacing DNA polymerase which lacks 5'→3' exonuclease activity (e.g., Sequencing Grade Taq from Promega or exo⁻ Vent or exo⁻ Deep Vent from New England BioLabs) in the PCR. The detector oligonucleotide signal primers hybridize to the target downstream from the PCR amplification primers, are displaced and are rendered double-stranded essentially as described for SDA. In PCR any RERS may optionally be selected for use in the detector oligonucleotide, as there are typically no modified deoxynucleoside triphosphates present which might induce nicking rather than cleavage of the RERS. As thermocycling is a feature of amplification by PCR, the restriction endonuclease is preferably added at low temperature after the final cycle of primer annealing and extension for end-point detection of amplification. However, a thermophilic restriction endonuclease that remains active through the high temperature phases of the PCR reaction could be present during amplification to provide a real-time assay. As in SDA systems, separation of the dye pair reduces fluorescence quenching, with a change in a fluorescence parameter such as intensity serving as an indication of target amplification.

The change in fluorescence resulting from unfolding or linearizing of the detector oligonucleotides may be detected at a selected endpoint in the reaction. However, because linearized secondary structures are produced concurrently with hybridization or primer extension, the change in fluorescence may also be monitored as the reaction is occurring, i.e., in "real-time". This homogeneous, real-time assay format may be used to provide semiquantitative or quantitative information about the initial amount of target present. For example, the rate at which fluorescence intensity changes during the unfolding or linearizing reaction (either as part of target amplification or in non-amplification detection methods) is an indication of initial target levels. As a result, when more initial copies of the target sequence are present, donor fluorescence more rapidly reaches a selected threshold value (i.e., shorter time to positivity). The decrease in acceptor fluorescence similarly exhibits a shorter time to positivity, detected as the time required to reach a selected minimum value. In addition, the rate of change in fluorescence parameters during the course of the reaction is more rapid in samples containing higher initial amounts of target than in samples containing lower initial amounts of target (i.e., increased slope of the fluorescence curve). These or other measurements as is known in the art may be made as an indication of the presence of target or as an indication of target amplification. The initial amount of target is typically determined by comparison of the experimental results to results for known amounts of target.

Assays for the presence of a selected target sequence according to the methods of the invention may be performed in solution or on a solid phase. Real-time or endpoint homogeneous assays in which the detector oligonucleotide functions as a primer are typically performed in solution. Hybridization assays using the detector oligonucleotides of the invention may also be performed in solution (e.g., as homogeneous real-time assays) but are also particularly well-suited to solid phase assays for real-time or endpoint detection of target. In a solid phase assay, detector oligonucleotides may be immobilized on the solid phase (e.g., beads, membranes or the reaction vessel) via internal or terminal labels using methods known in the art. For example, a biotin-labeled detector oligonucleotide may be immobilized on an avidin-modified solid phase where it will produce a change in fluorescence when exposed to the target under appropriate hybridization conditions. Capture of the target in this manner facilitates separation of the target from the sample and allows removal of substances in the sample that may interfere with detection of the signal or other aspects of the assay. An example of a solid phase system that can be used is an electronic microarray, i.e., an active programmable electronic matrix hybridization system.

A simplified version of the active programmable electronic matrix hybridization system for use with this invention is described as follows. Generally, a substrate supports a matrix or array of electronically addressable microlocations. A permeation layer is disposed above the individual electrodes. The permeation layer permits transport of relatively small charged entities through it, but precludes large charged entities, such as DNA from contacting the electrodes directly. The permeation layer avoids the electrochemical degradation that would occur in the DNA by direct contact with the electrodes. It further serves to avoid the strong, non-specific adsorption of DNA to electrodes. Attachment regions are disposed upon the permeation layer and provide for specific binding sites for target materials.

In operation, a reservoir comprises that space above the attachment regions that contains the desired (as well as undesired) materials for detection, analysis or use. Charged entities, such as charged DNA, are located within the reservoir. In one aspect, the active, programmable matrix system comprises a method for transporting the charged material to any of the specific microlocations. When activated, a microlocation generates the free field electrophoretic transport of any charged, functionalized, specific binding entity towards the electrode. For example, if one electrode were made positive and a second electrode negative, electrophoretic lines of force would run between two electrodes. The lines of electrophoretic force cause transport of charged binding entities that have a net negative charge toward the positive electrode. Charged materials having a net positive charge move under the electrophoretic force toward the negatively charged electrode. When the net negatively charged binding entity that has been functionalized contacts the attachment layer as a result of its movement under electrophoretic force, the finctionalized specific binding entity becomes covalently attached to the attachment layer corresponding to the first electrode.

Electrophoretic transport generally results from applying a voltage, which is sufficient to permit electrolysis and ion transport within the system. Electrophoretic mobility results, and current flows through the system, such as by ion transport through the electrolyte solution. In this way, a complete circuit may be formed via the current flow of the ions, with the remainder of the circuit being completed by the conventional electronic components, such as the electrodes and controlled circuitry. For example, for an aqueous electrolyte solution containing conventional material such as sodium chloride, sodium phosphate, buffers and ionic species, the voltage which induces electrolysis and ion transport is greater than, or equal to, approximately 1.2 volts.

It is possible to protect the attachment layers that are not subject to reaction by making their corresponding electrodes negative. This results in electrophoretic lines of force emanating from such attachment regions. The electrophoretic force lines serve to drive away negatively charged binding entities from the non-reactant attachment layer and towards the attachment layer corresponding to the first electrode. In this way, "force field" protection is formed around the attachment layers that it is desired to have nonreactive with the charged molecules at that time.

One highly advantageous result of this system is that charged binding materials may be highly concentrated in regions adjacent to the signal attachment layers. For example, if an individual microlocation is positively charged, and the remaining microlocations are negatively charged, the lines of electrophoretic force will cause transport of the net negatively charged binding entities toward the positively charged microlocation. In this way, a method for concentrating and reacting analytes or reactants at any specific microlocation on the device may be achieved. After the attachment of the specific binding entities to the attachment layer, the underlying microelectrode may continue to function in a direct current (DC) mode. This unique feature allows relatively dilute charged analytes or reactant molecules free in solution to be transported rapidly, concentrated, and reacted in a serial or parallel manner at any specific microlocation that is maintained at the opposite charge to the analyte or reactant molecules. This ability to concentrate dilute analyte or reactant molecules at selected microlocations greatly accelerates the reaction rates at these microlocations.

After the desired reaction is complete, the electrode may have its potential reversed, thereby creating an electrophoretic force in the direction opposite the prior attractive force. In this way, nonspecific analytes or unreacted molecules may be removed from the microlocation. Specific analytes or reaction products may be released from any microlocation and transported to other locations for further analysis, stored at other addressable locations, or removed completely from the system. This removal or deconcentration of materials by reversal of the field enhances the discrimination ability of the system by resulting in removal of nonspecifically bound materials. By controlling the amount of now-repulsive electrophoretic force to nonspecifically bound materials on the attachment layer, electronic stringency control may be achieved. By raising the electric potential at the electrode so as to create a field sufficient to remove partially hybridized DNA sequences, thereby permitting identification of single mismatched hybridizations, point mutations may be identified.

Operations may be conducted in parallel or in series at the various attachment layers. For example, a reaction may occur first at a first attachment layer, utilizing the potentials as shown. The potential at a first electrode may be reversed, that is, made negative, and the potential at the adjacent second electrode may be made positive. In this way, a series reaction occurs. Materials that were not specifically bound to the first attachment layer would be transported by electrophoretic force to the attachment layer. In this way, the concentration aspect is utilized to provide high concentrations at that specific attachment layer then subject to the positive electrophoretic force. The concentrated materials may next be moved to an adjacent, or other, attachment layer. Alternatively, multiple attachment layers may be deprotected in the sense that there is a net electrophoretic force field emanating from the electrode through the attachment layer out into the reservoir. By deprotecting the multiple attachment layer, multiplex reactions are performed. Each individual site may serve in essence as a separate biological "test tube" in that the particular environment addressed by a given attachment layer may differ from those environments surrounding the other attachment layers.

In one embodiment, the permeation layer contains avidin and one of the SDA primers contains biotin. Subsequent to amplification, the amplicons are electronically addressed onto the array and binds to the avidin. One or more labeled detector probes are then added and allowed to hybridize with the amplicons. The presence of hybridized detector probes is then detected. In a second embodiment, one or more capture probes are designed to hybridize with the amplified nucleic acid. Each capture probe contains biotin and is either bound onto or electronically addressed and bound onto an array in which the permeation layer contains avidin. The amplicons are then electronically addressed onto the array and hybridize with the capture probes. One or more labeled detector probes are then added and allowed to hybridize with the amplicons. The presence of hybridized detector probes is then detected.

Further details of the electronic microarray and associated systems are described by Heller et al. (1997, U.S. Pat. No. 5,605,662; 1997, U.S. Pat. No. 5,682,957; 1997, PCT published application No. WO97/12030), and Sosnowski et al. (1998, PCT published application No. WO98/10273), the disclosures of which are hereby specifically incorporated herein by reference.

In addition, techniques utilizing SDA and electronic microarrays, including several assay formats, are disclosed in copending application Ser. No. 09/290,632, filed concurrently herewith, incorporated herein by reference. In one embodiment, described in this application, a sandwich assay is used in which a single-stranded capture probe is electronically deposited on the array, and serves to capture one strand of a charged molecule such as target nucleic acid or amplicon thereof. A multiplicity of molecules such as nucleic acid capture probes can be electronically deposited on different pads of the array. It is preferred that the hybridization of the target molecule or amplicon and the capture probe be conductd electronically. Following capture of the charged molecule to the capture sites, the captured molecule may be detected by a labeled reporter probe that binds to the captured molecule.

In a second embodiment described in this application, an electronic amplification is conducted on the microarray. In this embodiment, target nucleic acid is electronically concentrated in the vicinity of anchored primers located on a capture site and used in an SDA or other amplification method. Electronic hybridization is used to hybridize the template molecules to the anchored SDA primers. The microchips are then incubated with an SDA reaction mix which contains the SDA components other than the template and the amplification primers. After the reaction is stopped, the products are denatured, and the microchip incubated with reporter probes to detect the presence of target nucleic acid. These embodiments illustrate that (a) the amplification may be conducted on an electronic microarray followed by analysis or (b) the amplification may be conducted in solution and then analysis conducted on an electronic microarray.

EXAMPLES

The following Examples illustrate specific embodiments of the invention described herein. As would be apparent to skilled artisans, various changes and modifications are possible, and are contemplated within the scope of the invention described.

Example 1

Primer Screening

All pairwise combinations of upstream and downstream amplification primers shown in Table I were tested for amplification of the target. Amplification reactions were conducted in the presence of 0, $10^3$ or $10^6$ genomic equivalents of Shigella DNA. Amplification was performed at 52° C. in buffers containing final concentrations of the following components: 30–40 mM potassium phosphate (pH 7.6), 5–9% glycerol, 3–7% dimethylsulfoxide (DMSO), 5 mM magnesium acetate, 700 ng human placental DNA, 10 µg acetylated bovine serum albumin, 1.82% trehalose, 0.36 mM dithiothreitol, 500 nM tSDA primers, 50 nM bumper primers, 0.25 mM dUTP, 0.7 mM 2'-deoxycytidine 5'-O-(1-thiotriphosphate), 0.1 mM dATP, 0.1 mM dGTP, and approximately 640 units BsoBI and 40 units Bst polymerase.

In brief, target DNA was denatured for 5 minutes at 95° C. and cooled to room temperature prior to addition to buffer containing the primers and bumpers. Incubation was continued at room temperature for 20 minutes, followed by incubation at 70° C. for 10 minutes to minimize potential false priming. Amplification was then initiated at 52° C. by transfer of a fixed volume of the priming mix to microtiter wells containing the amplification enzymes. Amplification was carried out for 1 hour at a constant temperature of 52° C. Amplification products were detected by autoradiography following primer extension with $^{32}$P-labeled detector sequence SEQ ID NO:10 and resolution on 8% denaturing polyacrylamide gels. Specific amplification products were detected with the following combinations of amplification primers: SEQ ID NO:1 and SEQ ID NO:4, SEQ ID NO:1 and SEQ ID NO:5, SEQ ID NO:1 and SEQ ID NO:6, SEQ ID NO:2 and SEQ ID NO:5, SEQ ID NO:3 and SEQ ID NO:4, SEQ ID NO:3 and SEQ ID NO:5, and SEQ ID NO:3 and SEQ ID NO:6.

Example 2

Determination of Analytical Sensitivity

SDA was performed as described in Example 1 using amplification primers SEQ ID NO:1 and SEQ ID NO:5 and bumper primers SEQ ID NO:7 and SEQ ID NO: 8 in buffer containing 30 mM potassium phosphate, 9% glycerol and 3% DMSO. Target DNA was included at 0, $10^2$, $10^3$ or $10^4$ genomic equivalents per reaction. An analytical sensitivity of $10^2$ was demonstrated through the detection of specific amplification products in reactions containing this level of input target.

Example 3

Evaluation of Primer Specificity

Primer specificity was evaluated using SEQ ID NO:1, SEQ ID NO:5, SEQ ID NO:7 and SEQ ID NO:8 as described in Example 1 with SDA buffer containing final concentrations of 30 mM potassium phosphate, 9% glycerol and 3% DMSO. Seventy-two strains of Shigella representing all four species within the genus and seven strains of EIEC were tested at $10^4$–$10^5$ genomic equivalents per reaction (Table 2). Seventy-one strains of Shigella yielded specific product as did all seven strains of EIEC for a calculated specificity of 99%.

TABLE 2

Shigella/EIEC Specificity Panel

| | Species | Strain |
|---|---|---|
| 1 | S. boydii | ATCC 12027 |
| 2 | S. boydii | ATCC 12031 |
| 3 | S. boydii | ATCC 12032* |
| 4 | S. boydii | ATCC 12034 |
| 5 | S. boydii | ATCC 12035 |
| 6 | S. boydii | ATCC 25930 |
| 7 | S. boydii | ATCC 35964 |
| 8 | S. boydii | ATCC 35965 |
| 9 | S. boydii | ATCC 35966 |
| 10 | S. boydii | ATCC 49812 |
| 11 | S. boydii | ATCC 8702 |
| 12 | S. boydii | ATCC 8704 |
| 13 | S. boydii | ATCC 9207 |
| 14 | S. boydii | ATCC 9210 |
| 15 | S. boydii | ATCC 9905 |
| 16 | S. dysenteriae | ATCC 9361 |
| 17 | S. dysenteriae | ATCC 9750 |
| 18 | S. dysenteriae | BDMS 2896 |
| 19 | S. dysenteriae | BDMS 2932 |
| 20 | S. dysenteriae | BDMS 2933 |
| 21 | S. dysenteriae | BDMS 2943 |
| 22 | S. dysenteriae | BDMS 2947 |
| 23 | S. dysenteriae | BDMS 3197 |
| 24 | S. dysenteriae | BDMS 3198 |
| 25 | S. dysenteriae | BDMS 3205 |
| 26 | S. dysenteriae | BDMS 9945 |
| 27 | S. dysenteriae | BDMS 9946 |
| 28 | S. flexneri | ATCC 11836 |
| 29 | S. flexneri | ATCC 12022 |
| 30 | S. flexneri | ATCC 12023 |
| 31 | S. flexneri | ATCC 12025 |
| 32 | S. flexneri | ATCC 49070 |
| 33 | S. flexneri | ATCC 9199 |
| 34 | S. flexneri | ATCC 9204 |
| 35 | S. flexneri | ATCC 9380 |
| 36 | S. flexneri | ATCC 9473 |
| 37 | S. flexneri | ATCC 9748 |
| 38 | S. flexneri | ATCC 9906 |
| 39 | S. flexneri | JHU 17628 |
| 40 | S. flexneri | JHU 21431 |
| 41 | S. flexneri | JHU 24929 |
| 42 | S. flexneri | JHU 24997 |
| 43 | S. flexneri | VTU 982-6065 |
| 44 | S. flexneri | VTU 982-6068 |
| 45 | S. flexneri | VTU 982-6103 |
| 46 | S. flexneri | VTU 982-6208 |
| 47 | S. flexneri | VTU 982-6250 |
| 48 | S. sonnei | ATCC 25931 |
| 49 | S. sonnei | ATCC 29029 |
| 50 | S. sonnei | ATCC 9290 |
| 51 | S. sonnei | BDMS 2888 |
| 52 | S. sonnei | BDMS 2894 |
| 53 | S. sonnei | BDMS 2928 |
| 54 | S. sonnei | BDMS 2948 |
| 55 | S. sonnei | BDMS 2949 |
| 56 | S. sonnei | BDMS 4424 |
| 57 | S. sonnei | BDMS 5701 |
| 58 | S. sonnei | BDMS 5702 |
| 59 | S. sonnei | BDMS 5704 |
| 60 | S. sonnei | BDMS 7140 |
| 61 | S. sonnei | BDMS 8154 |
| 62 | S. sonnei | BDMS 8996 |
| 63 | S. sonnei | BDMS 9108 |
| 64 | S. sonnei | BDMS 9490 |
| 65 | S. sonnei | BDMS 9921 |
| 66 | S. sonnei | VTU 982-6211 |
| 67 | S. sonnei | VTU 982-6227 |
| 68 | S. sonnei | VTU 982-6244 |
| 69 | S. sonnei | VTU 982-6246 |
| 70 | S. sonnei | VTU 982-6247 |
| 71 | S. sonnei | VTU 982-6259 |
| 72 | S. sonnei | VTU 982-6262 |
| 73 | E. coli 0124:B17:H | ATCC 12806 |
| 74 | E. coli 0124 | L-73C-7 |
| 75 | E. coli 028 | D-233 |

TABLE 2-continued

Shigella/EIEC Specificity Panel

| | Species | Strain |
|---|---|---|
| 76 | E. coli 0144:H25 | EI-1109 |
| 77 | E. coli 029:H | EI-1150 |
| 78 | E. coli 0136 | CW-139-8 |
| 79 | E. coli 0136 | U-346 |

*Negative by SDA for ipaH target sequence

Example 4

Evaluation of Cross-Reactivity

Cross-reactivity was evaluated using the primers and reaction conditions described in Example 3. Non-Shigella/EIEC organisms were tested at $10^7$ genomic equivalents per reaction. Negative results were obtained with all 25 organisms tested (Table 3). In each case, when $10^4$ copies of Shigella target DNA were seeded into the reaction, specific product was obtained indicating that the non-Shigella/EIEC DNA did not inhibit amplification.

TABLE 3

Shigella/EIEC Cross-Reactivity Panel

| | Species | | Strain |
|---|---|---|---|
| 1 | Actinomyces israelii | Serotype 1 | ATCC 10049 |
| 2 | Arcobacter butzleri | | ATCC 49616 |
| 3 | Arcobacter cryaerophilus | | ATCC 49942 |
| 4 | Bacteroides ureolyticus | | ATCC 33387 |
| 5 | Campylobacter coli | | ATCC 49941 |
| 6 | Campylobacter jejuni | | ATCC 49943 |
| 7 | Campylobacter lari | | ATCC 43675 |
| 8 | Candida albicans | | ATCC 44808 |
| 9 | Citrobacter freundii | | ATCC 8090 |
| 10 | Enterobacter cloacae | | ATCC 13047 |
| 11 | Enterococcus faecalis | | ATCC 29212 |
| 12 | Escherichia coli 055 | | ATCC 12014 |
| 13 | Escherichia coli 0157:H7 | non-SLTI | T-3785 |
| 14 | Escherichia coli | | T-4025 |
| 15 | Helicobacter pylori | | ATCC 43526 |
| 16 | Klebsiella pneumoniae | subsp. pneumoniae | ATCC 13883 |
| 17 | Proteus mirabilis | | ATCC 29906 |
| 18 | Salmonella enteritidis | | ATCC 13076 |
| 19 | Salmonella minnesota | | ATCC 9700 |
| 20 | Salmonella typhimurium | | ATCC 13311 |
| 21 | Staphylococcus aureus | subsp aureus | ATCC 12598 |
| 22 | Streptococcus bovis | | ATCC 9809 |
| 23 | Streptococcus pyogenes | Group A | ATCC 19615 |
| 24 | Vibrio cholerae | Biotype El Tor | ATCC 14035 |
| 25 | Yersinia enterocolitica | | ATCC 9610 |

Example 5

Electronic Microarray Analysis

The microelectronic array assembly has been described previously (R. G. Sosnowski et al., 1997, *Proc. Natl. Acad. Sci. USA* 94:119–123). Electronic targeting of capture probes, amplicons or detector probes utilized conditions reported elsewhere (R. G. Sosnowski et al., 1997, *Proc. Natl. Acad Sci. USA* 94:119–123; C. F. Edman et al., 1997, *Nucleic Acids Res.* 25:4907–4914). The permeation layer of the microelectronic array assembly advantageously contains avidin. In brief, capture probes are electronically addressd onto a microelectronic array. Crude amplification reactions are either spun for 2 min through G6 columns (Biorad, Hercules, Calif.) preequilibrated with distilled water or dialyzed in multiwell plates (Millipore, Bedford, Mass.) for $\geq 5$ hrs against distilled water. The prepared samples are then mixed in a 1:1 ratio with 100 mM histidine and heated at 95° C. for 5 min prior to electronic addressing. For detection, a fluorescent labeled oligonucleotide (detector probe) is introduced in 6×SSC and allowed to hybridize for 30 min at room temperature. The array is then washed in 0.1×STE/1%SDS followed by 1×STE. The presence of detector probe is then detected.

While the invention has been described with some specificity, modifications apparent to those of ordinary skill in the art may be made without departing from the scope of the invention. Various features of the invention are set forth in the following claims.

What is claimed is:

1. An oligonucleotide consisting of a target binding sequence selected from the group consisting of the target binding sequences of ShH1AL48 (SEQ ID NO:1), ShH1AL46 (SEQ ID NO:2), SbH1AL44 (SEQ ID NO:3), of ShH1AR50 (SEQ ID NO:4), ShH1AR46 (SEQ ID NO:5) and ShH1AR42 (SEQ ID NO:6), and optionally, a sequence required for an amplification reaction.

2. The oligonucleotide of claim 1 wherein the sequence required for the amplification reaction is a restriction endonuclease recognition site which is nicked by a restriction endonuclease during Strand Displacement Amplification.

3. The oligonucleotide of claim 2 selected from the group consisting of ShH1AL48 (SEQ ID NO:1), ShH1AL46 (SEQ ID NO:2), ShH1AL44 (SEQ ID NO:3), of ShH1AR50 (SEQ ID NO:4), ShH1AR46 (SEQ ID NO:5) and ShH1AR42 (SEQ ID NO:6).

4. An oligonucleotide consisting of ShH1BL44 (SEQ ID NO:7) or ShH1BBR44 (SEQ ID NO:8).

5. An oligonucleotide selected from the group consisting of Sh1DL44 (SEQ ID NO:9), a nucleic acid complementary to SEQ ID NO:9, Sh1DR46 (SEQ ID NO:10) and a nucleic acid complementary to SEQ ID NO: 10.

6. The nucleic acid of claim 5 wherein said nucleic acid comprises a detectable marker.

7. The nucleic acid of claim 6 wherein said detectable marker is selected from the group consisting of a radioactive marker and a fluorescence marker.

8. A pair of amplification primers comprising:
a) a first primer consisting of a target binding sequence selected from the group consisting of the target binding sequences of ShH1AL48 (SEQ ID NO:1), ShH1AL46 (SEQ ID NO:2), ShH1AL44 (SEQ ID NO:3), and, optionally, a sequence required for an amplification reaction, and;
b) a second primer consisting of a target binding sequence selected from the group consisting of the target binding sequences of ShH1AR50 (SEQ ID NO:4), ShH1AR46 (SEQ ID NO:5) and ShH1AR42 (SEQ ID NO:6), and, optionally, a sequence required for an amplification reaction.

9. The pair of amplification primers of claim 8 wherein the sequence required for the amplification reaction is a restriction endonuclease recognition site which is nicked by a restriction endonuclease during Strand Displacement Amplification.

10. The pair of amplification primers of claim 9 wherein said first primer is selected from the group consisting of ShH1AL48 (SEQ ID NO:1), SbH1AL46 (SEQ ID NO:2), ShH1AL44 (SEQ ID NO:3) and said second primer is selected from the group consisting of ShH1AR50 (SEQ ID NO:4), ShH1AR46 (SEQ ID NO:5) and ShH1AR42 (SEQ ID NO:6).

11. The pair of amplification primers of claim 9 wherein said first primer is ShH1AL48 (SEQ ID NO:1) and said second primer is ShH1AR46 (SEQ ID NO:5).

* * * * *

SEQUENCE LISTING

<160> NUMBER OF SEQ ID NOS: 10

<210> SEQ ID NO 1
<211> LENGTH: 40
<212> TYPE: DNA
<213> ORGANISM: Artificial Sequence
<220> FEATURE:
<223> OTHER INFORMATION: Description of Artificial Sequence:Primer
      for SDA of Shigella spp./EIEC

<400> SEQUENCE: 1
cgattccgct ccagacttct cgggtcagaa gccgtgaaga                40

<210> SEQ ID NO 2
<211> LENGTH: 39
<212> TYPE: DNA
<213> ORGANISM: Artificial Sequence

```
<220> FEATURE:
<223> OTHER INFORMATION: Description of Artificial Sequence:Primer
      for SDA of Shigella spp./EIEC

<400> SEQUENCE: 2
cgattccgct ccagacttct cgggtcagaa gccgtgaag                              39

<210> SEQ ID NO 3
<211> LENGTH: 38
<212> TYPE: DNA
<213> ORGANISM: Artificial Sequence
<220> FEATURE:
<223> OTHER INFORMATION: Description of Artificial Sequence:Primer
      for SDA of Shigella spp./EIEC

<400> SEQUENCE: 3
cgattccgct ccagacttct cgggcagaag ccgtgaag                               38

<210> SEQ ID NO 4
<211> LENGTH: 39
<212> TYPE: DNA
<213> ORGANISM: Artificial Sequence
<220> FEATURE:
<223> OTHER INFORMATION: Description of Artificial Sequence:Primer
      for SDA of Shigella spp./EIEC

<400> SEQUENCE: 4
accgcatcga agtcatgtct cggggccatg gtccccaga                              39

<210> SEQ ID NO 5
<211> LENGTH: 38
<212> TYPE: DNA
<213> ORGANISM: Artificial Sequence
<220> FEATURE:
<223> OTHER INFORMATION: Description of Artificial Sequence:Primer
      for SDA of Shigella spp./EIEC

<400> SEQUENCE: 5
accgcatcga agtcatgtct cgggcatggt ccccagag                               38

<210> SEQ ID NO 6
<211> LENGTH: 37
<212> TYPE: DNA
<213> ORGANISM: Artificial Sequence
<220> FEATURE:
<223> OTHER INFORMATION: Description of Artificial Sequence:Primer
      for SDA of Shigella spp./EIEC

<400> SEQUENCE: 6
accgcatcga agtcatgtct cgggcatggt ccccaga                                37

<210> SEQ ID NO 7
<211> LENGTH: 13
<212> TYPE: DNA
<213> ORGANISM: Artificial Sequence
<220> FEATURE:
<223> OTHER INFORMATION: Description of Artificial Sequence:Bumper
      primer for SDA of Shigella spp./EIEC

<400> SEQUENCE: 7
gcactgccga agc                                                          13

<210> SEQ ID NO 8
<211> LENGTH: 15
<212> TYPE: DNA
<213> ORGANISM: Artificial Sequence
<220> FEATURE:
```

-continued

```
<223> OTHER INFORMATION: Description of Artificial Sequence:Bumper
      primer for SDA of Shigella spp./EIEC

<400> SEQUENCE: 8
gcttcagtac agcat                                                15

<210> SEQ ID NO 9
<211> LENGTH: 15
<212> TYPE: DNA
<213> ORGANISM: Artificial Sequence
<220> FEATURE:
<223> OTHER INFORMATION: Description of Artificial Sequence:Detecto
      r probe for Shigella spp./EIEC

<400> SEQUENCE: 9
gaatttacgg actgg                                                15

<210> SEQ ID NO 10
<211> LENGTH: 16
<212> TYPE: DNA
<213> ORGANISM: Artificial Sequence
<220> FEATURE:
<223> OTHER INFORMATION: Description of Artificial Sequence:Detecto
      r probe for Shigella spp./EIEC

<400> SEQUENCE: 10
gaaccagtcc gtaaat                                               16
```